United States Patent [19]
Jones et al.

[11] Patent Number: 5,980,978
[45] Date of Patent: Nov. 9, 1999

[54] FORMATION OF A METALORGANIC COMPOUND FOR GROWING EPITAXIAL SEMICONDUCTOR LAYERS

[75] Inventors: Anthony Copeland Jones, Prescot; Simon Andrew Rushworth, Wirral; Trevor Martin, Malvern; Timothy John Whittaker, Malvern; Richard William Freer, Malvern, all of United Kingdom

[73] Assignee: The Secretary of State for Defence in Her Britannic Majesty's Government of the United Kingdom of Great Britain and Northern Ireland of Defence Evaluation and Research Agency, Worcestershire, United Kingdom

[21] Appl. No.: 08/793,810

[22] PCT Filed: Sep. 4, 1995

[86] PCT No.: PCT/GB95/02089

§ 371 Date: Jul. 14, 1997

§ 102(e) Date: Jul. 14, 1997

[87] PCT Pub. No.: WO96/07661

PCT Pub. Date: Mar. 14, 1996

[30] Foreign Application Priority Data

Sep. 2, 1994 [GB] United Kingdom .................... 9417707
Apr. 28, 1995 [GB] United Kingdom .................... 9508702

[51] Int. Cl.⁶ .................................................. C23C 16/18
[52] U.S. Cl. .............................. 427/96; 427/99; 427/123; 427/124; 427/229; 427/252; 117/103; 117/104

[58] Field of Search .................... 257/565; 427/248.1, 427/252, 229, 96, 99, 123, 124; 117/103, 104; 556/1, 121, 170, 187

[56] References Cited

U.S. PATENT DOCUMENTS

| 4,464,233 | 8/1984 | Mullin et al. ...................... 204/59 QM |
| 4,604,473 | 8/1986 | Cole-Hamilton et al. .................. 556/1 |
| 4,812,586 | 3/1989 | Mullin et al. ............................ 556/129 |

FOREIGN PATENT DOCUMENTS

460598 A1 12/1991 European Pat. Off. .

OTHER PUBLICATIONS

Abernathy, Solid–State Electronics, vol. 38, No. 3, pp. 737–738, May 1995.
Freer et al., Advanced Materials, vol. 7, No. 5, pp. 478–481, May 1995.
Inorganic Chemistry, vol. 7, No. 6, Jun. 3, 1986, Henrickson, C.H. et al., "Lewis Acidity of Alanes. Interactions of Trimethylalane with Amines, Ethers, and Phosphines," pp. 1047–1051.
Journal of Chemical Society, Dalton Transactions, vol. 1, 1988, Foster D.F., et al., "Synthesis and Thermal Properties of Adduicts of Trimethylindium with Nitrogen–containing Lewis Bases," pp. 7–11 (no month).

Primary Examiner—Timothy Meeks
Attorney, Agent, or Firm—Howell & Haferkamp, L.C.

[57] ABSTRACT

Semiconductor devices are prepared by growth of epitaxial layers on a substrate from metalorganic compounds of the formula $MR_3$, R being an alkyl group, or its amine adduct. The metalorganic compound was prepared by reacting a Grignard reagent with a metal halide in an amine solvent.

24 Claims, 2 Drawing Sheets

FORMATION OF A METALORGANIC COMPOUND FOR GROWING EPITAXIAL SEMICONDUCTOR LAYERS

CROSS-REFERENCE TO RELATED APPLICATIONS

This application is the National Stage of International Patent Application No. PCT/GB95/02089, filed Sep. 4, 1995; which claims priority from Great Britain Application GB94107707.8, filed Sep. 2, 1994 and Great Britain Application GB9508702.9, filed Apr. 28, 1995.

BACKGROUND OF THE INVENTION

This invention concerns semiconductor devices and their production.

While there is a considerable interest in InP/InGaAs devices grown by chemical beam epitaxy (CBE), particularly in the area of selective growth, the GaAs/AlGaAs material system is less well established. With the exception of very encouraging data for heterojunction bipolar transistors (HBT's) and high eletron mobility transistors (HEMTS's) the quality of AlGaAs alloys grown by CBE have generally been inferior to those grown by metalorganic vapor phase epitaxy (MOVPE) or molecular beam epitaxy (MBE). The degradation of material quality results from unintentional moieties of group III metal alkyls and also unintentional oxygen incorporation. Much effort has, therefore, gone into the development of new precursors which reduce unintentional impurity incorporation in epitaxial AlGaAs layers.

A direct correlation has been established between oxygen concentrations unintentionally incorporated into AlGaAs grown by CBE and trace quantities of diethylether detected by in-situ modulated beam mass spectrometry (MBMS) in the group III metalorganic precursors. The trace ether is residual from the synthesis of the metal trialkyl $MR_3$, which involves the alkylation of the metal trihalide by a Grignard reagent RMgX carried out in an ether solvent. Subsequent purification processes are then performed to remove the oxygen containing ether solvent and other impurities from the metalorganic precursor. However, these processes are never entirely successful.

For example, U.S. Pat. No. 4,464,233 describes the formation of dimethylmagnesium by reacting a Grignard reagent with a metal halide using electrolysis, having tetra (n-butyl) ammonium percholate as an ionizable support electrolyte and a solvent such as an aliphatic ether, cyclic aliphatic mono- or poly- ether or a non-cyclic ether. Similarly, U.S. Pat. No. 4,604,473 discloses a method of producing a trialkylgallium compound by reacting a gallium trihalide with a Grignard reagent in the presence of an ether.

Trimethylindium compounds with nitrogen-containing Lewis-bases have also been prepared using Lewis-base solvents, such as diethyl ether (see Journal of the Chemical Society, Dalton Transactions vol. 1. 1998, USA; Foster et al: "synthesis and thermal properties of trimethylindium with nitrogen-containing Lewis bases") and the interaction of, for example, ethers and amines with trimethylalane adducts is discussed in Inorganic Chemistry vol. 7, no. 6., Jun. 3, 1986, USA pages 1047–1051; C. H. Henrickson et al.

Alternative methods for producing metalorganic precursors for use in the deposition of epitaxial layers have been described in, for example, U.S. Pat. No. 4,812,586 and EP0460598.

BRIEF SUMMARY OF THE INVENTION

A first object of this invention is to provide a method of growing semiconductor layers in which the above-mentioned oxygen impurity problem is eliminated or at least reduced in effect.

A second object of this invention is to provide semiconductor devices in which the above-mentioned oxygen impurity problem is eliminated or at least reduced in effect.

According to a first aspect of the invention there is provided a method of growing semiconductor layers on a substrate comprising the steps of delivering to the substrate, a metalorganic compound of the formula $MR_3$, R being an alkyl group, prepared by reacting a Grignard reagent with a metal halide, and causing deposition on the substrate of metal from the metalorganic compound, characterised in that reaction of the Grignard reagent with the metal halide is carried out in an amine solvent.

According to a second aspect of the invention there is provided a semiconductor device comprising a layer grown on a substrate from a metalorganic compound of the formula $MR_3$, wherein the metalorganic compound is prepared by reacting a Grignard reagent with the metal halide characterized in that said reaction is carried out in an amine solvent.

DETAILED DESCRIPTION OF THE INVENTION

Figure 1:
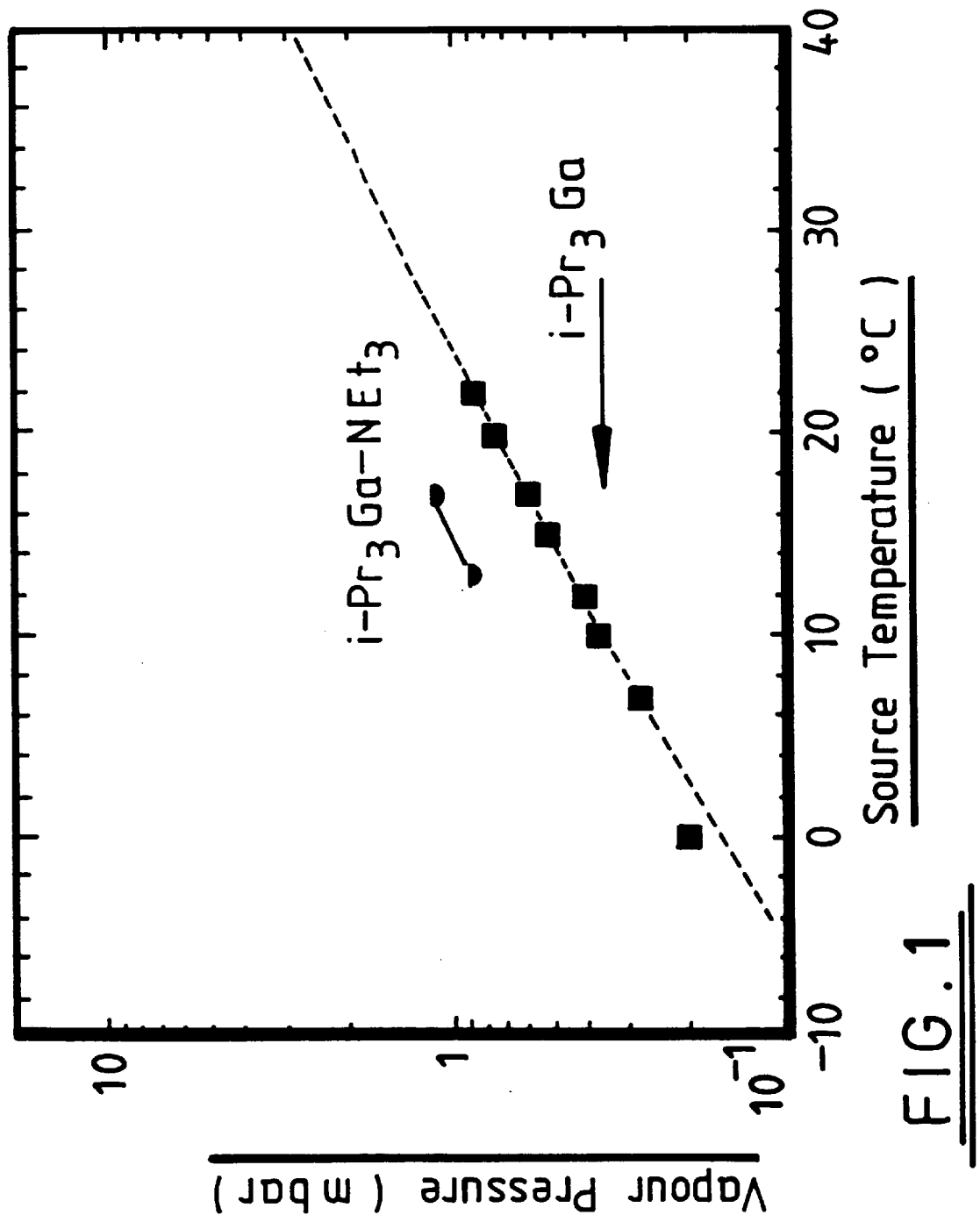
FIG. 1 is a plot of vapor pressure versus source temperature for preparation of a tri-isopropyl gallium adduct according to the method of the invention (solid line) and by a conventional method (dashed line)

The Grignard reagent for use in preparing the metalorganic compound is preferably prepared in an amine solvent, especially the amine to be used in preparing the metalorganic compound.

The amine is preferably a tertiary amine such as, for example, a tertiary alkyl amine or a tertiary heterocyclic amine. Amines for use in the preparation of the metalorganic compound and/or the Grignard reagent are preferably liquid at room temperature typically 18 to 20° C. Preferred tertiary alkyl amines have the formula

wherein $R^1$, $R^2$ and $R^3$ are alkyl groups having from 1 to 4 carbon atoms and wherein $R^1$, $R^2$ and $R^3$ may be the same or two of $R^1$, $R^2$ and $R^3$ may be the same. Preferred amines for use in the invention are triethylamine and dimethylethylamine.

Suitable heterocylic amines for use in the invention may include pyridine, 2H-pyrrole, pyrimidine, pyrazine, pyridazine, 1,3,5-triazine and hexahydrotriazine.

The process for preparing the metalorganic compound can result in an amine adduct which may be used in the method of the invention instead of the metalorganic compound alone.

Suitable metalorganic amine adducts have the formula $MR_3 \cdot A$ wherein M is a metal, R is an alkyl group and A is a tertiary amine such as a tertiary alkyl amine of the formula

wherein $R^1$, $R^2$ and $R^3$ are as defined above or a tertiary heterocyclic amine.

The Grignard reagent may be prepared in any suitable way, typically by reaction of magnesium with an alkyl halide, wherein the alkyl group is that required for the metalorganic compound.

The preparation of metalorganic compounds and metalorganic amine adducts preferably follows the following sequence of steps:
1. Synthesis of RMgX in $NR_3$ solvent;
2. Suspension of $MCl_3$ in pentane;
3. Addition of RMgX to $MCl_3$ in $NR_3$/pentane;
4. Removal of volatiles and isolation of $MR_3(NR_3)$ by distillation;
5. Removal of volatile impurities from $MR_3(NR_3)$;
6. Isolation of the adduct or thermal dissociation of $MR_3(NR_3)$ and removal by fractional distillation of the $NR_3$ ligand.

Metalorganic compounds that may be useful in the invention include alkyl compounds of Group II, Group III and Group V metals. Examples of such compounds include dialkyl zinc, dialkyl cadmium, trialkyl aluminium, trialkyl gallium, trialkyl indium, trialkyl phosphorus, trialkyl arsenic and trialkyl antimony.

The formation of an amine permits the removal of volatile metallic and non-metallic microimpurities from the metalorganic compound. Impurities may be readily removed from the adduct by distillation. The adduct may be split by removal of the amine, such as by heating, to provide the metalorganic compound alone for some purposes, such as a precursor for MOVPE or CBE. Alternatively the adduct itself may be used as a precursor for the deposition of, for example Group III–V or II–VI layers, such as gallium arsenide, aluminium gallium arsenide and zinc selenide, by MOVPE, CBE and other vapour phase epitaxy techniques.

In general the method of the invention may be used for the growth of Group III–V semiconductor device structures. The method of the invention generally encompasses all vapour phase growth techniques, such as, for example; MOVPE, CBE and MOMBE.

The method of the invention may be used in the production of semiconductor devices for electronic applications e.g. transistors (FET, HEMT and HBT devices), diodes, superlattice current emitters and mixer diodes. Photonic application devices may also be produced e.g. lasers (vertical cavity (VCSEL) and planar), light emitting diodes, reflectors and modulators (including those used as part of the VCSEL, photodetectors, photodiodes and optical waveguides.

Integration of any of the above using selective growth techniques may be used to achieve lateral integration e.g. for lasers and waveguides.

The method of the invention may further be used to produce deposits in Group II-VI devices for e.g. long wavelength infra red detectors and sources. The method of the invention may be further used to produce metal coatings e.g. for Al, Ga and In deposition.

AlGaAs layers may be produced by vapour phase deposition, especially by chemical beam epitaxy, of a trialkyl gallium amine adduct, typically of trisopropyl gallium with an AlH amine adduct and arsine.

The method of the invention may be used in, for example, low temperature organometallic vapour phase epitaxy of InSb preferably using tri-isopropyl antimony as the precursor. Typically tri-isopropyl antimony and trimethylindium are used to grow InSb epilayers on GaAs. Similarly GaSb may be grown by MOVPE from tri-isopropyl antimony and trimethylgallium.

In one preferred method of the invention the metalorganic compound is delivered under high vacuum to a substrate without carrier gas and pyrolysed on the substrate. The metalorganic compound or its amine adduct may be used. The substrate is typically a Group III to V single crystal such as of gallium arsenide. This method may be especially suitable for deposition of Group III metal especially gallium and especially from triisopropyl gallium.

Antimony may also be deposited on a substrate in a similar way but may also be deposited as may other metals from metalorganic compounds or their amine adducts using MOVPE techniques in which a carrier gas is used to transport the metalorganic vapour at pressures typically in the range of 2 to 760 Torr to the substrate, such as a single crystal Group III to V substrate, where it is pyrolysed to form the desired layer.

Typical semiconductor devices which may be made using the invention include CD lasers and high speed transistors.

The invention will now be further described by means of the following examples. Each reaction described below was carried out in an atmosphere of dry/oxygen-free dinitrogen using reagents which had been dried and deoxygenated by standard purification methods.

EXAMPLE 1

This example demonstrates the production of triisopropylgallium using triethylamine as solvent.

A solution of iso-propyl magnesium bromide, i-PrMgBr, in triethylamine was prepared by the dropwise addition of iso-propyl bromide, i-PrBr (280 g, 2.3 mol) to a stirred suspension of magnesium metal turnings (60 g, 2.5 mol) in triethylamine, $NEt_3$ (1000 cm$^3$). This resulted in a vigorous exothermic reaction. It was found that this reaction could be more easily initiated by the addition of a crystal of iodine. After complete addition of the i-PrBr, the reaction mixture was stirred at ambient temperature for 4 hours.

A solution of gallium trichloride, $GaCl_3$ (125 g, 0.7 mol) in pentane (500 cm$^3$) was then added slowly with stirring to the solution of i-PrMgBr in $NEt_3$. This led to an exothermic reaction. After complete addition of the $GaCl_3$-pentane solution, the reaction mixture was stirred for 4 hours at room temperature to ensure complete reaction.

After removal of volatiles by distillation in vacuo, the crude product was isolated by vacuum distillation (100° C.) into a receiver cooled in liquid nitrogen (ca −196° C.). Volatile impurities were removed from the crude product by distillation in vacuo (25–50° C.) and the pure liquid product was obtained by vacuum distillation (80° C.) into a cooled receiver (ca −106° C.).

The metalorganic product was identified using proton NMR spectroscopy as a triethylamine adduct of triisopropylgallium, i-$Pr_3Ga(NEt_3)_{0.6}$.

The proton NMR data are summarised below:

| (ppm) | (Assignment) |
|---|---|
| 0.8 (triplet, 5.4H) | NCH$_2$C$\underline{H}_3$ |
| 1.0 (multiplet, 3H) | GaC$\underline{H}$(CH$_3$)$_2$ |
| 1.4 (doublet, 18H) | GaCH(C$\underline{H}_3$)$_2$ |
| 2.4 (quartet, 3.6H) | NC$\underline{H}_2$CH$_3$ |

The i-Pr$_3$Ga-NEt$_3$ adduct was further analysed for trace metal impurities using inductively coupled plasma emission spectroscopy (ICP-ES). The only impurities detected were silicon (0.03 ppm w.r.t. Ga) and zinc (0.2 ppm w.r.t. Ga).

Yield i-Pr$_3$Ga(NEt$_3$)$_{0.6}$=49.4 g.

The vapour pressure of the iPr$_3$Ga adduct was found to be 0.9 mBar ar 13° C.

The tri-isopropyl gallium prepared in the above way was used to grow a layer of AlGaAs on a gallium arsenide substrate by chemical beam epitaxy under the following conditions:

Substrate temperature—540° C.

AlGaAs growth rate 1/hr

Group V precursor—thermally cracked arsine

Group III precursors—tri-isopropyl gallium triethylamine adduct plus AlH$_3$-NMe$_2$Et An AlGaAs layer (aluminium composition of 18%) grown in this manner demonstrated oxygen levels of less than $4 \times 10^{16}$ cm$^{-3}$ (as measured by secondary ion mass spectrometry, SIMS). This layer is superior to an AlGaAs layer (aluminium composition of 25%) grown using triisopropylgallium synthesised in a conventional manner (i.e. using an ether solvent), and AlH$_3$(NMe$_2$Et), in which much higher oxygen levels of $9 \times 10^{16}$ cm$^{-3}$ were detected by SIMS. The AlGaAs layer grown using the triisopropyl gallium-triethylamine adduct was comparable in oxygen content (<4×16 cm$^{-3}$) with the best layers thus far obtained using triethylgallium and AlH$_3$(NMe$_2$Et) under identical CBE growth conditions.

Figure 2:
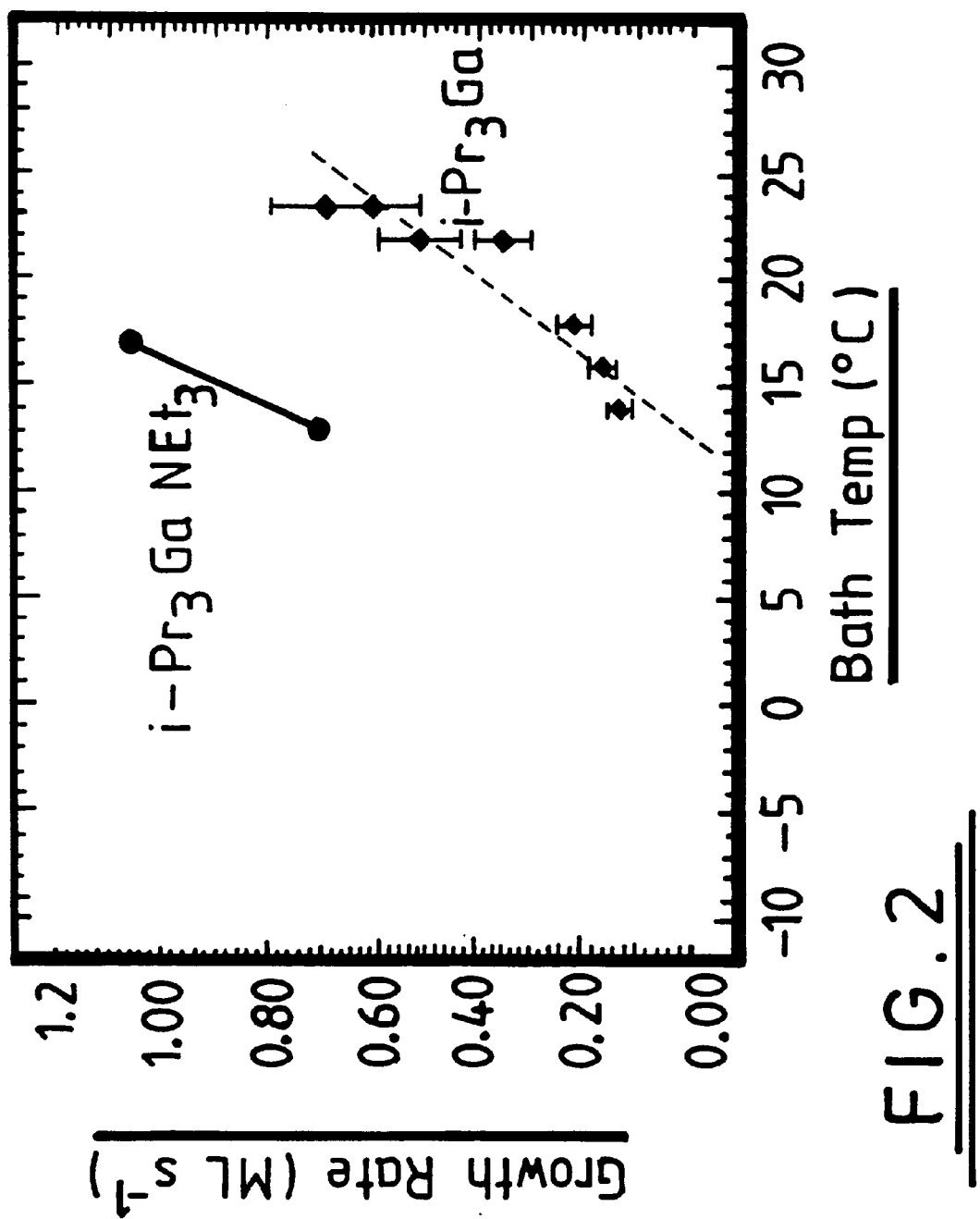
FIG. 2 is a plot of growth rate versus bath temperature for preparation of a tri-isopropyl gallium adduct according to the method of the invention (solid line) and by a convention method (dashed line).

FIGS. 1 and 2 respectively of the accompanying drawings show comparison of vapour pressures and growth rates of the tri-isopropyl gallium adduct prepared according to this Example and tri-isopropyl gallium prepared in the conventional way. As can be seen the adduct has both higher vapour pressures and growth rates which are advantageous for chemical vapour deposition processes.

EXAMPLE 2

This demonstrates the production of tri-isopropylgallium using dimethylethylamine as solvent.

A solution of iso-propylmagnesium bromide, i-PrMgBr, in dimethylethylamine was prepared by the dropwise addition of iso-propylbromide, i-PrBr (166 g, 1.4 mol) to a stirred suspension of Mg metal turnings (48 g, 2.0 mol) in dimethylethylamine, NMe$_2$Et (500 cm$^3$). This resulted in a vigorous exothermic reaction which could be more easily initiated by the addition of a small quantity of iodine. After complete addition of the i-PrBr the reaction mixture was stirred at room temperature for 4 hours.

A solution of GaCl$_3$ (69 g, 0.4 mol) in pentane (260 cm$^3$) was then added slowly, with stirring, to the solution of i-PrMgBr in NMe$_2$Et. This led to a vigorous exothermic reaction. After complete addition of the GaCl$_3$-pentane solution, the reaction mixture was stirred for 4 hours at room temperature to ensure complete reaction.

After removal of volatiles by atmospheric pressure distillation (60° C.), the crude product was isolated by vacuum distillation (100° C.) into a cooled receiver (ca –196° C.).

Volatile impurities were removed from the crude products in vacuo, and the pure liquid product was obtained by reduced pressure distillation (70° C.) into a receiver.

The metalorganic product was identified using proton NMR spectroscopy as the dimethylethylamine adduct of triisopropylgallium, i-Pr$_3$Ga(NMe$_2$Et). The proton NMR data are summarised below:

| (ppm) | (Assignment) |
|---|---|
| 0.6 (triplet, 3H) | NCH$_2$C$\underline{H}_3$ |
| 0.9 (multiplet, 3H) | GaC$\underline{H}$(CH$_3$)$_2$ |
| 1.4 (doublet, 18H) | GaCH(C$\underline{H}_3$)$_2$ |
| 1.9 (singlet, 6H) | NC$\underline{H}_3$ |
| 2.4 (quartet, 2H) | NC$\underline{H}_2$CH$_3$ |

The i-Pr$_3$Ga-NMe$_2$Et adduct was further analysed for trace metal impurities using ICP-ES. The only impurities detected were silicon (0.2 ppm w.r.t Ga) and Zinc (4.6 ppm w.r.t Ga).

Yield i-Pr$_3$Ga(NMe$_2$Et)=58.5 g

EXAMPLE 3

This example demonstrates the production of tri-isopropylindium using triethylamine as solvent.

A solution of i-PrMgBr in NEt$_3$ was prepared by the dropwise addition of i-PrBr (72 g,0.6 mol) in NEt$_3$ (200 cm$^3$). This led to a vigorous exothermic reaction. After complete addition of the i-PrBr the reaction mixture was stirred at room temperature for 4 hours.

The solution of i-PrMgBr in NEt$_3$ was added dropwise, with stirring, to a suspension of indium trichloride, InCl$_3$ (35 g, 0.2 mol) in NEt$_3$(200 cm$^3$). This led to an exothermic reaction. After complete addition of the i-PrMgBr/NEt$_3$ solution, the reaction mixture was boiled under reflux for 2 hours.

After removal of volatiles by distillation in vacuo, the crude product was obtained by vacuum distillation (100° C.) into a cooled receiver (ca –196° C.). Volatile impurities were removed from the crude product by distillation in vacuo and the pure liquid product was obtained by vacuum distillation (70° C.) into a cooled receiver (ca –196° C.).

The metalorganic product was identified using proton NMR spectroscopy as a triethylamine adduct of triisopropylindium, i-Pr$_3$In(NEt$_3$). The proton NMR data are summarised below:

| (ppm) | (Assignment) |
|---|---|
| 0.8 (triplet, 9H) | NCH$_2$C$\underline{H}_3$ |
| 1.1 (multiplet, 3H) | InC$\underline{H}$(CH$_3$)$_2$ |
| 1.6 (doublet, 18H) | InCH(C$\underline{H}_3$)$_2$ |
| 2.4 (quartet, 6H) | NC$\underline{H}_2$CH$_3$ |

The i-Pr$_3$In-NEt$_3$ adduct was further analysed for trace metal impurities using ICP-ES. The only impurities detected were silicon (0.04 ppm w.r.t In) and zinc (3.8 ppm w.r.t In).

Yield i-Pr$_3$In(NEt$_3$)=8 g.

EXAMPLE 4

This example demonstrates the production of triisopropylindium using dimethylethylamine as solvent.

A solution of i-PrMgBr in NMe$_2$Et was prepared by the dropwise addition of i-PrBr (192 g, 1.6 mol) to a stirred suspension of Mg metal turnings (56 g, 2.3 mol) in NMe$_2$Et (400 cm$^3$).

This resulted in a vigorous exothermic reaction. After complete addition of the i-PrBr the reaction mixture was stirred for 4 hours at room temperature.

The solution of i-PrMgBr in NMe$_2$Et was added dropwise, with stirring, to a suspension of InCl$_3$ (72 g, 0.3 mol) in pentane. This resulted in an exothermic reaction. After complete addition of the i-PrMgBr/NMe$_2$Et solution, the reaction mixture was boiled under reflux for 2 hours.

After removal of volatiles by atmospheric pressure distillation, (60° C.), the crude product was obtained by reduced pressure distillation (85–90° C.) into a receiver. Volatile impurities were removed from the crude product by vacuum distillation (25° C.).

The pure liquid product was obtained by vacuum distillation (85–90° C.) into a receiver cooled to approx. −196° C.

The straw yellow liquid was identified using proton NMR spectroscopy as the dimethylethylamine adduct of tri-isopropyl indium, iPr$_3$In(NMe$_2$Et). The proton NMR data are summarised below:

| (ppm) | (Assignment) |
|---|---|
| 0.8 (triplet, 3H) | NCH$_2$C$\underline{H}$$_3$ |
| 1.0 (multiplet, 3H) | InC$\underline{H}$(CH$_3$)$_2$ |
| 1.5 (doublet, 18H) | InCH(C$\underline{H}$$_3$)$_2$ |
| 2.0 (singlet, 6H) | NC$\underline{H}$$_3$ |
| 2.3 (quartet, 2H) | NC$\underline{H}$$_2$CH$_3$ |

The i-Pr$_3$In-NMe$_2$Et adduct was further analysed for trace metal impurities using ICP-EAS. The only impurities detected were silicon (<1 ppm w.r.t In), and Zn(0.12 w.r.t In).

Yield i-Pr$_3$In(NMe$_2$Et)=81.7 g.0

We claim:

1. A method of growing a semiconductor layer on a substrate comprising the steps of:
    delivering to the substrate, a metalorganic compound of the formula MR$_3$, M being a metal and R being an alkyl group, prepared by reacting a Grignard reagent with a metal halide, and
    causing deposition on the substrate of the metal from the metalorganic compound, wherein reaction of the Grignard reagent with the metal halide is carried out in an amine solvent.

2. A method as claimed in claim 1, wherein the metalorganic compound is used for said deposition in the form of amine adduct.

3. A method as claimed in claim 1, wherein the Grignard reagent is prepared in an amine solvent.

4. A method as claimed in claim 3, wherein the amine solvent used in preparing the Grignard reagent is the same as that used for the reaction thereof with the metal halide.

5. A method as claimed in claim 1, wherein the amine is a tertiary amine.

6. A method as claimed in claim 5, wherein the amine is selected from the group consisting of tertiary alkyl amines and tertiary heterocyclic amines.

7. A method as claimed in claim 1, wherein the amine is liquid at room temperature.

8. A method as claimed in claim 1, wherein the amine has the following general formula:

wherein R$^1$, R$^2$ and R$^3$ are alkyl groups having from 1 to 4 carbon atoms and wherein R$^1$, R$^2$ and R$^3$ are the same or two of R$^1$, R$^2$ and R$^3$ are the same.

9. A method as claimed in claim 1, wherein the amine is selected from the group consisting of triethylamine and dimethylethylamine.

10. A method as claimed in claim 1, wherein the amine is selected from the group consisting of pyridine, 2H-pyrrole, pyrimidine, pyrazine, 1,3,5-triazine and hexahydrotriazine.

11. A method as claimed in claim 1, wherein the Grignard reagent is prepared by reaction of magnesium with an alkyl halide, the alkyl group thereof being that required for the metalorganic compound.

12. A method as claimed in claim 1, wherein the metalorganic compound is selected from the group consisting of trialkyl aluminium, trialkyl gallium, trialkyl indium, trialkyl phosphorus, trialkyl arsenic and trialkyl antimony.

13. A method as claimed in claim 1, wherein the alkyl groups are isopropyl groups.

14. A method as claimed in claim 1, wherein the metalorganic compound is used for said deposition in the form of amine adduct having the formula:

MR$_3$.A wherein M is a metal;

R is an alkyl group; and

A is a tertiary heterocyclic amine or is a tertiary alkyl amine of the formula:

where R$^1$, R$^2$ and R$^3$ are alkyl groups having from 1 to 4 carbon atoms and wherein R$^1$, R$^2$ and R$^3$ are the same or two of R$^1$, R$^2$ and R$^3$ are the same.

15. A method as claimed in claim 14, wherein the alkyl group of the MR$_3$is a C$_{1-5}$ straight or branched chain alkyl group.

16. A method as claimed in claim 14, wherein the alkyl group of the MR$_3$ is an isopropyl group.

17. A method as claimed in claim 1, wherein the metalorganic compound or its amine adduct is delivered as a vapour to the substrate and pyrolysed thereon.

18. A method as claimed in claim 1, wherein the substrate is a Group III–V single crystal.

19. A method as claimed in claim 18, wherein the substrate is gallium arsenide.

20. A method as claimed in claim 18, wherein the metalorganic compound is trialkyl gallium.

21. A method as claimed in claim 18, wherein the metalorganic compound is triisopropyl gallium.

22. A method as claimed in claim 1, wherein the metalorganic compound is triisopropyl gallium which is delivered to the substrate with a Group V element precursor to form a layer having a gallium and the Group V element.

23. A method as claimed in claim 22, wherein a Group III precursor in addition to the triisopropyl gallium is also delivered to the substrate.

24. A method as claimed in claim 22, wherein the Group V precursor is arsine and a second Group III precursor is also delivered to the substrate, the second Group III precursor being an AlH$_3$ amine adduct.

* * * * *